United States Patent [19]

Clark

[11] Patent Number: 5,714,345
[45] Date of Patent: Feb. 3, 1998

[54] INCREASED EXPRESSION OF A GENE BY A SECOND TRANSFERRED MAMMARY GLAND SPECIFIC SEQUENCE TRANSGENIC

[75] Inventor: Anthony John Clark, Midlothian, Great Britain

[73] Assignee: Pharmaceutical Proteins Limited, Edinburgh, Scotland

[21] Appl. No.: 472,737

[22] Filed: Jun. 6, 1995

Related U.S. Application Data

[63] Continuation of Ser. No. 81,315, Jul. 19, 1993, abandoned.

[30] Foreign Application Priority Data

Dec. 24, 1990 [GB] United Kingdom ............... 9028062

[51] Int. Cl.$^6$ ............... C12N 15/63; C12N 15/16; C12N 15/79
[52] U.S. Cl. ............... 435/69.1; 435/172.3; 435/317.1; 935/111; 800/2
[58] Field of Search ............... 800/2, DIG. 1, 800/DIG. 4; 435/172.3, 317.1; 935/111

[56] References Cited

U.S. PATENT DOCUMENTS

| | | | |
|---|---|---|---|
| 5,221,778 | 6/1993 | Byrne et al. | 800/2 |
| 5,322,775 | 6/1994 | Clark et al. | 435/69.1 |

FOREIGN PATENT DOCUMENTS

| | | |
|---|---|---|
| 0 420 055 | 4/1991 | European Pat. Off. |
| WO 88/00239 | 1/1988 | WIPO. |
| WO 90/05188 | 5/1990 | WIPO. |
| WO 90/06363 | 6/1990 | WIPO. |
| WO 90/07936 | 7/1990 | WIPO. |
| WO 90/13645 | 11/1990 | WIPO. |
| WO 91/0666 | 5/1991 | WIPO. |
| WO 91/13151 | 9/1991 | WIPO. |
| WO 91/15111 | 10/1991 | WIPO. |

OTHER PUBLICATIONS

Kappel et al., Curr. Opin. Biotech. 3:548–53 (1992).
Clark et al., Biotechnology 7:487–492 (1989).
Archibald et al., Proc. Natl. Acad. Sci. USA, 87:5178–5182 (1990).
Wilmut et al., News Scientist, 7 Jul. 1988, pp. 56–59.
Van Brunt, BioTechnology 6(10):1149–1154 (1988).
Wilmut et al., "Production of pharmaceutical proteins in milk", Experientia 47: 905–912 (1991).

Primary Examiner—Jasemine C. Chambers
Assistant Examiner—Karen M. Hauda
Attorney, Agent, or Firm—Seidel, Gonda, Lavorgna & Monaco, PC

[57] ABSTRACT

Transgenic animals capable of expressing a desired protein can be prepared by co-introducing into an egg or embryo cell of an animal, a first sequence, which encodes the desired protein, and a second, more efficiently expressed, DNA sequence. Expression efficiency is thereby conferred on the first sequence, leading to improved yield or targeting, or both. Co-introduction may be achieved by co-injecting a mixture of the two DNA sequences into a fertilized egg, in the case of an animal. The invention can be used to enhance the efficiency of expression of desired proteins, such as those having pharmaceutical activity in the mammary gland of a female transgenic animal.

12 Claims, 12 Drawing Sheets

BAD  *FIG. 7A*
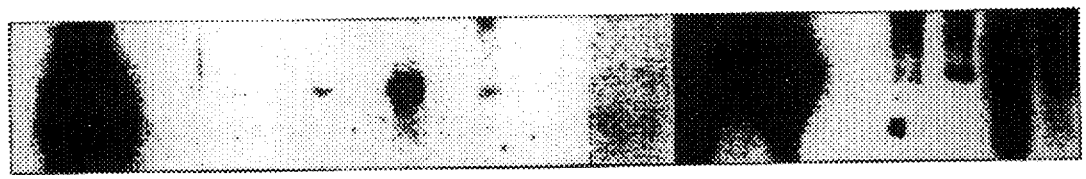
BLG  *FIG. 7B*
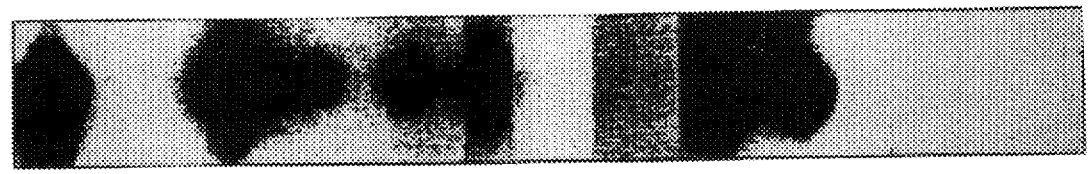

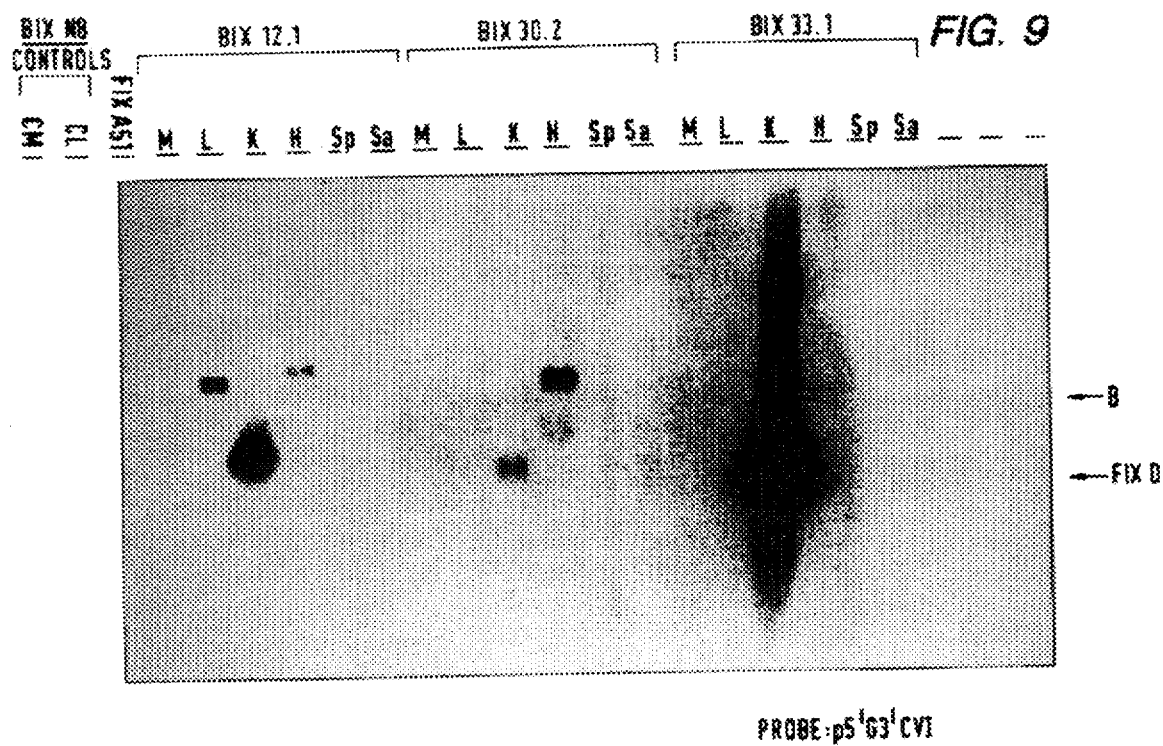

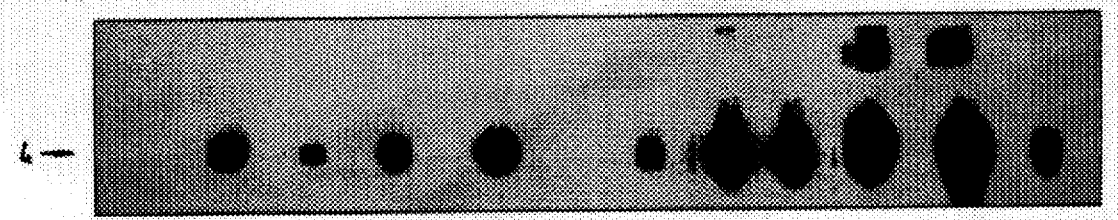
FIG. 10A
FIG. 10B

INCREASED EXPRESSION OF A GENE BY A SECOND TRANSFERRED MAMMARY GLAND SPECIFIC SEQUENCE TRANSGENIC

This is a continuation of application Ser. No. 08/081,315 filed Jul. 19, 1993, now abandoned.

This invention relates to the production of transgenic organisms, DNA preparations useful in such a method and transgenic animals and plants produced thereby.

Transgenic animals for a number of purposes have been developed and work on their further development continues. Among their uses, transgenic animals offer a powerful approach for the production of recombinant proteins. In particular, as is disclosed in WO-A-8800239, the expression of genes encoding a protein of interest can be targeted to the mammary gland of transgenic farm animals such as sheep, goats or cattle, and the protein product can be harvested from their milk.

The use of transgenic animals for protein production in milk necessitates foreign genes being introduced into the germ line in such a way that their expression can be directed to the mammary gland. Targeting of expression to other organs or tissues is important in transgenic animals prepared for other purposes. Introduction of foreign genes into an animal's germ line has been demonstrated in WO-A-8800239, which describes the production of transgenic sheep carrying genes designed to express human Factor IX and human $\alpha_1$-antitrypsin in milk. In order to direct expression of these transgenes to the mammary gland, the approach taken was to take regulatory sequences from milk protein genes and fuse them to the protein coding sequences of the product of interest. In practice, this has involved the use of transgenic mice as a model system to assess the performance of the various hybrid gene constructs; the much shorter generation time of mice enables experiments to be undertaken within a realistic time-scale. For a genetic construct to be useful, it must express in the chosen model system at a reasonable frequency and at suitable levels.

A number of genomic milk protein genes which an be regarded as natural (that is to say the same configuration as DNA sequences found in the genome of animals from which the genes were isolated; such isolated gene may be termed genomic clones and will usually contain introns) have been shown to express relatively efficiently in transgenic mice. Reference is made in particular to Example 7 of WO-A-8800239, which relate to the expression of the gene coding ovine β-lactoglobulin in transgenic mice. Other examples include the systems of Vilotte et al (*Eur. J. Biochem.* 186 43–48 (1989)) and Bayna et al *Nuc. Acids. Res.* 18 2977–2985 (1990)). These genomic clones thus appear to contain all the essential regulatory sequences required for directing expression efficiently to the mammary gland.

A number of hybrid genes comprising milk protein gene regulatory elements fused to DNA sequences encoding proteins of interest have also been assessed in transgenic mice; in WO-A-8800239 the proteins of interest were human Factor IX and human $\alpha_1$-antitrypsin. In many cases such as this, however, the level of expression of the hybrid genes is well below that which would be optimal for commercial purposes. A common feature of such relatively poorly expressing constructs is that they were constructed using contiguous cDNA sequences and therefore lacked their natural introns. This problem was addressed and overcome in WO-A-9005188, which disclosed the use of a construct comprising a genomic sequence encoding an exogenous protein and constaining some, but not all, of its natural introns. Such a construct performed relatively efficiently.

In some circumstances, however, it may be wished to avoid including natural introns in a construct. First, the DNA sequences for many proteins of interest are available only as cDNA sequences; indeed, it may me much easier to prepare a cDNA sequences from a corresponding mRNA sequence transcribed in a given tissue in abundance in a target tissue than to isolate a genomic DNA. Secondly, some genes are very large, even if the proteins that they encode are not correspondingly large; too great a size makes the inclusion of most or all of the introns difficult as a practical matter.

There is therefore a need to enhance the efficiency of expression of a construct which normally expresses poorly as a transgene. Such poorly expressing constructs include, but are not limited to, those comprising cDNA sequences. The present invention relates to such a method and thereby provides a solution to at least some of the problems described above. While the invention has particular application to the production of transgenic animals, its use in the production of transgenic plant is also contemplated to solve comparable problems in their production.

According to a first aspect of the present invention, there is provided a process for the preparation of a transgenic animal or plant capable of expressing a first DNA sequence, the process comprising co-introducing into a cell or group of cells from which an animal or plant may be derived the first DNA sequence and a second DNA sequence, wherein the second DNA sequence is, when so introduced without the first sequence, capable of being expressed as, or regulating the expression of, a transgene with greater specificity and/or a greater frequency of expression and/or at a higher level than that at which the first sequence, without the second sequence, is capable of being expressed as a transgene, and allowing a transgenic animal or plant to develop from the cell(s).

The most commonly used method of introducing DNA into an animal cell for the purpose of transgenesis is injection (or microinjection, as it is sometimes termed). This is the method of choice for the production of trangenic animals by means of the present invention. Usually a few hundred linear molecules of DNA is directly microinjected into a pro-nucleus (often the male pro-nucleus) of a fertilised one cell egg; microinjected fertilised egg may then subsequently be transferred into the oviducts of pseudo-pregnant foster mothers and allowed to develop. The invention is however not limited to this method of introduction; any suitable method can be used. Egg or embryo cells may be used, as may embryonic stem (ES) cells.

Transgenic plants are usually currently prepared by different procedures. Preferably, DNA is transformed into plant cells using a disarmed Ti-plasmid vector and carrier by Agrobacterium by procedures known in the art, for example as described in EP-A-0116718 and EP-A-0270822. Alternatively, the foreign DNA could be introduced directly into plant cells using an electrical discharge apparatus. This method is preferred where Agrobacterium is ineffective, for example where the recipient plant is monocotyledenous. Any other method that provides for the stable incorporation of the DNA within the nuclear DNA of any plant cell of any species would also be suitable. Such methods include those suitable for species of plant which are not currently capable of genetic transformation.

It appears that introduction of DNA in the ways described above leads to integration (at least in a functional if not a structural sense) within the host's DNA in such a manner that the transgene becomes hereditable. Co-introduction may therefore lead to co-integration. Co-integration may take place in such a way that the first and second DNA sequence segregate together (i.e. co-segregate) in subsequent generations; this would be consistent with closely similar physical sites of integration in the genome.

The first and second DNA sequences are in one embodiment of the invention co-introduced by introducing a mixture of them (for example by injection, in the case of animal methodology) into the recipient cell. However, it is not necessary for the two sequences to be introduced simultaneously; instead, sequential introduction may be found to be acceptable in practice. Co-introduction may also be achieved by covalently or otherwise linking the first and second DNA sequences: the two sequences may be linked in a single DNA molecule. In this embodiment of the invention it is possible to tailor quite precisely the construct to be introduced; for example, a first sequence may be sandwiched between two second sequences, and/or the tandem nature of the sequences (i.e. whether they are head to head or head to tail) can be fixed.

A process of the first aspect of the invention can therefore be seen to involve the co-introduction of a relatively inefficient, but desired, transgene with a relatively efficiently expressing transgene; this may lead to co-integration at the same site in the chromosome or at sites near to one another.

The first DNA sequence may comprise cDNA or other DNA encoding the desired protein and, if the purpose of the transgene is expression, sufficient regulatory sequences (for example including a promoter) operatively linked to the protein-encoding DNA to direct the expression, for example in a target tissue or organ. In the case when expression is being targeted at the mammary gland of a mammal, the regulatory sequence may be derived from a milk protein, particularly a whey protein such as β-lactoglobulin, α-lactalbumin or whey acidic protein. The desired protein may be any protein (which term includes glycoprotein) sought to be and capable of being, produced in a transgenic. High value proteins, such as those having pharmaceutical activity, are particular candidates for use in the present invention. Example include, but are not limited to, insulin, plasminogen activators, $\alpha_1$-antitrypsin, blood factors such as Factor VIII and IX, Protein C and erythropoietin. The regulatory sequences used in association with the protein-coding DNA may be 5' and/or internal and/or 3' regulatory sequences.

The second DNA sequence is capable of being expressed, as a transgene, when introduced without the first sequence, with greater specificity and/or a greater frequency of expression and/or at a higher level (often a higher mean level) than that at which the first sequence alone is capable of being expressed. The second DNA sequence is therefore relatively efficiently expressed, compared to the first DNA sequence. A greater efficiency of expression may be achieved by a greater frequency of expression. A greater frequency of expression means a higher proportion of animals or plants or lines that now express the first sequence; this is clearly of importance both practically and economically.

The second sequence may be derived from or constituted by a gene, preferably complete with its associated regulatory sequences, normally expressed in the target organ. For example, if the target organ for expression is the mammary gland, the second DNA sequence is preferably derived from a milk protein gene, again particularly a whey protein gene such as β-lactoglobulin or α-lactalbumin or a casein gene such $\alpha S_1$-casein. The gene may be the same as that from which the regulatory sequences used in the first DNA sequence are derived. The second sequence may be an artificial construct or a normal gene.

Transgenes may be expressed in many organs of animals by means of this invention; the mammary gland is only one example. In plants, transgene expression may be specific for a particular tissue, if desired.

According to a second aspect of the invention, there is provided DNA useful for the preparation of a transgenic animal or plant expressing a first DNA sequence, the DNA comprising, on the same or separate molecules, the first sequence and a second DNA sequence, wherein the second DNA sequence is, when introduced as a transgene without the first sequence, capable of being expressed or regulating expression with greater specificity and/or with a greater frequency of expression and/or at a higher level than that at which the first sequence, when introduced as a transgene without the second sequence, is capable of being expressed.

The first and second DNA sequences may be embodied on the same DNA molecule, in which case the sequences may be regarded as covalently linked, with or without a linker sequence. Alternatively, the first and second DNA sequences may be provided on different DNA molecules. In this case, the DNA may take the form of a mixture of such molecules or a kit of separate preparations of the molecules.

The invention is not limited to the presence of a single first sequence and a single second sequence. A plurality of relatively inefficiently expressing first sequences may be potentiated by one or more relatively efficiently expressing second sequence, and a plurality of second sequences may potentiate one or more second sequences. It is preferred that the number of relatively efficiently expressing second sequences be present in excess, compared to the relatively inefficiently expressing first sequence. For example from 2 to 5 to 10 copies of the second sequence may be present per copy of the first sequence.

According to a third aspect of the invention, there is provided a transgenic animal or plant capable of expressing a first sequence as a transgene, the said animal or plant having the first sequence and a second sequence, wherein the second sequence is such that, when introduced as a transgene without the first sequence, it is capable of being expressed or regulating expression with greater specificity and/or with a greater frequency of expression and/or at a higher level than that at which the first sequence, when introduced as a transgene without the second sequence, is capable of being expressed.

In the case of animals, suitable species include those which are (a) practicable to work with and (b), if the objects is to use the invention for production of a desired molecule, are capable of giving sufficient yields for practical purposes. Small animals such as rodents including mice, rats, hamsters and guinea pigs may be suitable for some applicants; livestock animals such as cattle, sheep, goats and pigs may be preferred for others.

In the case of plants, the invention is applicable to a wide variety of species, both monocots and dicots, depending on the intended application.

Preferred features of the second and third aspects of the invention are as for the first aspect, *mutatis mutandis*.

The invention will now be illustrated by the following examples and contrasted with the comparative examples. The examples and comparative examples refer to the accompanying drawings, in which.

Figure 8A:
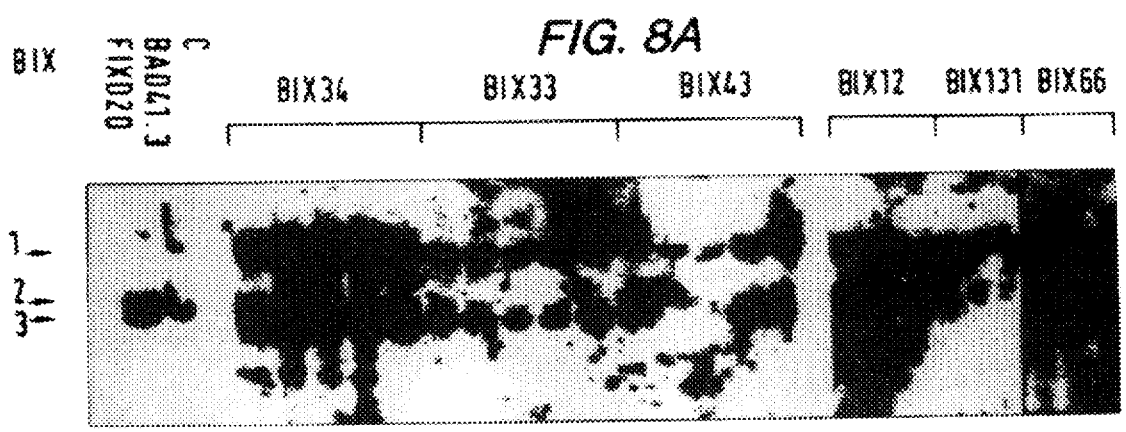
Figure 8B:
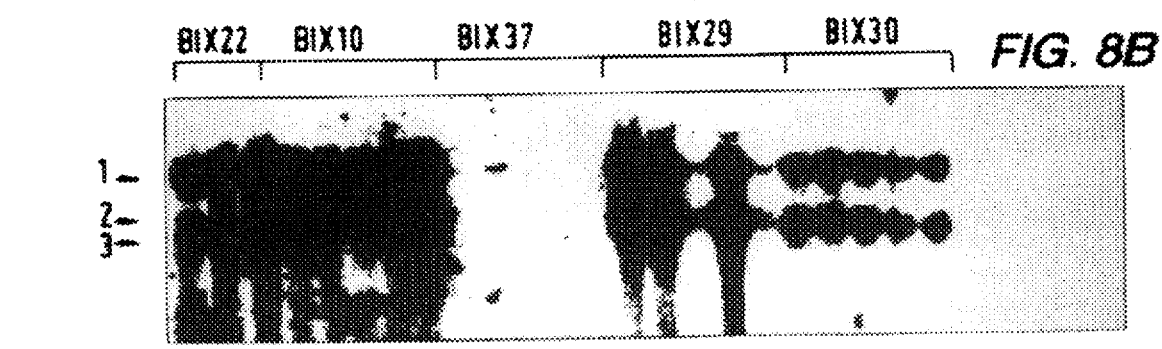
Figure 11:
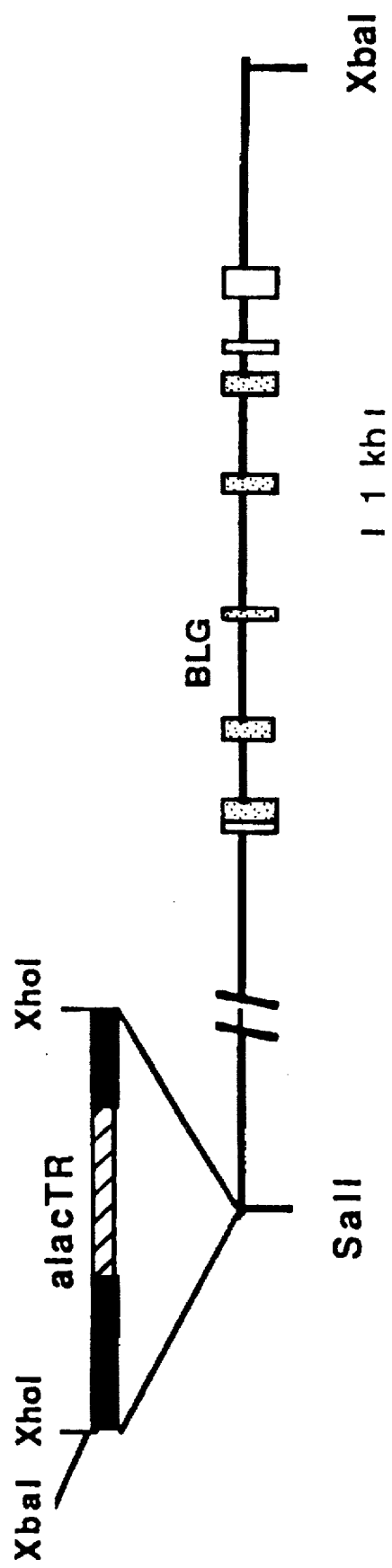

FIGS. 7a and 7b show a Northern blots showing the result of hybridisation experiments which reveal the presence of two transgenes in mice according to the invention; Band 1 is an AATD-specific transcript (~1600 nt); Band 2 is an AATB-specific transcript (~1400 nt); and Band 3 is a BLG-specific transcript (~800 nt);

FIGS. 8a and 8b are Southern blots showing the co-segregation of FIXD and BLG (Example 2); Band 1 is a BLG-specific band; Band 2 is a FIXD-specific band; and Band 3 is a non-specific junction band;

FIG. 9 shows the tissue-specific expression of FIXD in BIX lines (Example 2);

FIGS. 10a and 10b are Northern blots illustrating detection of FIXD and BLG transcripts in BIX mice; Band 1 is an endogenous mouse fIX transcript (~2600 nt); Band 2 is a BLG-FIX transcript in FIXA51; Band 3 is a FIXD transcript; and Band 4 is a BLG transcript; and FIG. 11 shows the construction of a β-lactoglobulin/ bovine α-lactalbumin construct (Example 3).

COMPARATIVE EXAMPLE 1

Where not specifically detailed, recombinant DNA and molecular biological procedures were after Maniatis et al ("Molecular Cloning" Cold Spring Harbor (1982) "Recombinant DNA" *Methods in Enzymology* Volume 68, (edited by R. Wu), Academic Press (1979); "Recombinant DNA part B" *Methods in Enzymology* Volume 100, (Wu, Grossman and Moldgave, Eds), Academic Press (1983); "Recombinant DNA part C" *Methods in Enzymology* Volume 101, (Wu, Grossman and Moldgave, Eds), Academic Press (1983); and "Guide to Molecular Cloning Techniques", *Methods in Enzymology* Volume 152 (edited by S. L. Berger & A. R. Kimmel), Academic Press (1987). Unless specifically stated, all chemicals were purchased from BDH Chemicals Ltd, Poole, Dorset, England or the Sigma Chemical Company, Poole, Dorset, England. Generally, all DNA modifying enzymes and restriction endonucleases were purchased from BCL, Boehringer Mannheim House, Bell Lane, Lewes, East Sussex BN7 1LG, UK.

[Abbreviations: bp=base pairs; kb=kilobase pairs, AAT= human $α_1$-antitrypsin; BLG=sheep β-lactoglobulin; FIX= factor IX; *E. coli*=*Escherichia coli*; dNTPs= deoxyribonucleotide triphosphates; restriction endonucleases are abbreviated thus e.g. BamHI; the addition of -O after a site for a restriction endonuclease e.g. PvuII-O indicates that the recognition site has been destroyed].

Preparation of Sheep Spleen DNA

Spleen tissue was procured from a freshly slaughtered Blackface/Suffolk lamb and nuclei were isolated essentially as described by Burch and Weintraub *Cell* 33 65 (1983). Nuclear pellets were lysed in 0.3M NaCl, 10 mM Tris.HCl, 10 mM EDTA, 1% SDS pH 7.4 and 400 μg/ml Proteinase K (Sigma Co, Fancy Road, Poole, Dorset BH17 7NH) and incubated for two hours at 37° C. Repeated phenol/ chloroform extractions were performed until the preparation was completely deproteinised. The DNA was ethanol precipitated and spool out using a glass rod, washed with 70% EtOH/30% TE (TE=10 mM Tris.HCl, 1 mM EDTA pH 8.0), dried in air and resuspended in TE to a concentration of 1 mg/ml.

Construction of Sheep DNA Lambda Fusion Genes

The lambda phage EMBL3 (Frischauf et al *J. Mol. Biol.* 170 827 (1983)) was employed to construct the genomic library. 30 μg of bacteriophage DNA were digested with 5-fold excesses of the restriction enzymes EcoRI and BamHI (supplied by Amersham International plc, Lincoln Place, Green End, Aylesbury, Buckinghamshire, England) using the conditions recommended by the manufacturer. After digestion, spermine hydrochloride was added to a concentration of 5 mM to precipitate the lambda DNA. After incubation for one hour on ice the DNA was pelleted at 10,000 g for 15 minutes in a bench microfuge, washed in 70% EtOH, 300 mM NaAc, 100 mM $MgCl_2$, repelleted and finally resuspended in TE at a concentration of 1 mg/ml.

Sheep DNA was partially digested with the restriction enzyme Sau3A (Amersham). 100 μg aliquots of the sheep DNA were digested with varying amounts of Sau3A [from 5-40 units] for 20 minutes at 37° C. The reactions were stopped by the addition of EDTA to 15 mM. The degree of digestion was assessed by electrophoresis on 0.6% agarose gels. Suitably digested samples were pooled and loaded onto 38.0 ml 10–40% sucrose gradients made up in 1M NaCl, 20 mM Tris.HCl 5 mM EDTA at pH 8.0. These gradients were centrifuged in a BECKMANN SW 28 rotor at 26,000 rpm for 24 hours. (The expression BECKMANN SW 28 is a trade mark). The sucrose gradients were fractionated from the top and 1 ml fractions collected. The size distribution of DNA molecules in each fraction was assessed by agarose gel electrophoresis, and fractions containing DNA molecules from 14–21 kb in size pooled. After a two-fold dilution in TE 2 volumes of EtOH were added and the DNA precipitated overnight at −20° C. The DNA was subsequently resuspended in TE to a concentration of 300 μg/ml.

7.5 μg of BamHI/EcoRI cut EMBL3 and 2.5 μg of sheep spleen DNA which had been partially digested with Sau3A were mixed together in 50 μl of a solution containing 60 mM Tris.HCl, 6 mM $MgCl_2$, 10 mM DTT, 0.01% gelatin, 0.25 mM rATP and 25 units of $T_4$ DNA ligase (Boehringer Company, Boehringer Mannheim House, Bell Lane, Lewes, East Sussex) and incubated overnight at 14° C.

After ligation 1 μg aliquots of the DNA were packaged in vitro using a kit purchased from Amersham following the recommended procedure of the manufacturer. The packaged library was titred on *E. coli* strain ED 8654. The estimated size of the library was $5.7×10^6$ plaque forming units (pfu). Immediately after titration, aliquots of the unamplified library were plated onto 10×22 $cm^2$ petri dishes (megaplates) using *E. coli* strain ED 8654 at a density of approximately 50,000 pfu/plate.

Screening the Lambda Genomic Library

Plaque-lifts the megaplates were performed according to the method of Benton and Davis (*Science* 196 180 (1977)) onto 20 $cm^2$ nitrocellulose membranes (Schleicher and Schull, Postfach 4, D-3354, Germany). A β-lactoglobulin cDNA clone (p931—gift of J. C. Mercier, INRA, Jouey-en-Josas, Paris) was nick translated with $^{32}P$ dCTP to a specific activity >$10^8$ dpm/mcg, by the method described by Rigby et al (*J. Mol. Biol.* 113 237 (1977)). β-lactoglobulin cDNA may be cloned as described by Mercier et al in *Biochimie* 67 959–971 (1985). The sequence of the p931 clone is given by Gaye et al in *Biochimie* 68, 1097–1107 (1986). Filters were prehybridised, hybridised and washed according to the method of Maniatis et al in *Cell* 15 687 (1978). The final wash was in 1×SET at 68° C. (SET is 0.15M NaCl, 2 mM EDTA, 0.3m Tris.HCl pH 8.0). Filters were blotted dry and spotted with $^{32}$P to orient them before exposure to X-ray film. Regions containing positively hybridising plaques were positioned on the megaplates by reference to the $^{32}$P spots picked using the sterile blunt end of a Pasteur pipette. The initial plaque lifts were titred on E. coli ED 8654 and plated onto 15 cm diameter Petri dishes at a plaque density of approximately 500/plate. These plates were rescreened by the procedures described above and individual positively hybridising plaques were picked using a toothpick into 1.0 ml of phage-buffer (phage buffer is 10 mM Tris.HCl, 10 mM MgCl$_2$, 0.01% gelatin, pH 7.4).

Preparation of Cloned β-Lactoglobulin DNA 0.4 ml of the resuspended phage solution was added to E. coli ED 8654 (Borg et al Mol. Gen. Genetics 146 199–207 (1976)) and plated out on 9 cm diameter Petri dishes to obtain confluent lysis of the bacterial lawn. Confluent plates were obtained from which the top plating agar was scraped off into 10 ml of phage buffer and incubated overnight with a few drops of chloroform. The bacterial debris was pelleted by centrifugation at 5000 rpm for five minutes and the phage stocks stored at 4° C. The stocks were titrated on E. coli ED 8654 to determine the pfu/ml figure.

$8 \times 10^7$ pfu were absorbed onto $7 \times 10^9$ E. coli cells in 10 ml of 10 mM MgSO$_4$ at 37° C. After 15 minutes, 2.5 ml aliquots were added to 100 ml L Broth/10 mM MgSO$_4$ in a one litre flask. The bacterial suspension was shaken vigorously for several hours and the OD$_{540}$ was monitored every hour. Lysis, as determined by a fall in the OD$_{540}$, occurred after several hours. When complete, 0.2 ml chloroform was added to each 100 ml culture and the culture left at 4° C. overnight.

The bacterial debris was removed by centrifugation at 10,000 rpm for 15 minutes. 10 µg/ml RNAse A and 10 µg/ml DNAse I were added to the supernatant which was then incubated at 37° C. for one hour. After this incubation NaCl was added to 40 g/litre and polyethylene glycol (PEG) to 10%. The preparation was cooled to 4° and left for at least two hours to precipitate the phage. The phage pellet was pelleted at 10,000 rpm for 15 minutes and resuspended in 16.0 ml of phage buffer. 8.0 ml of this suspension was layered upon a step gradient comprising 1.5 ml 56% CsCl, 1.5 ml 45% CsCl and 2.5 ml 31% CsCl (dissolved in phage buffer) in a 14.0 ml ultracentrifuge tube. The step gradients were centrifuged at 35,000 rpm for 1.5 hours in a swing-out rotor at 20° C. The phage band was removed with a needle and syringe and, to complete the purification of the phage particles, a second step gradient centrifugation was performed.

The purified phage particles were dialysed into 0.1M NaCl, 10 mM Tris.HCl, 1 mM EDTA pH 8.0 and then deproteinised by successive extractions with phenol and chloroform. NaCl was added to a final concentration of 0.3M and then the phage DNA precipitated by the addition of 2 volumes of EtOH. The DNA was pelleted by centrifugation at 10,000 rpm for 20 minutes, washed with 70% EtOH, 30% TE, dried and then resuspended in TE to a final concentration of 200–400 µg/ml.

Figure 1:
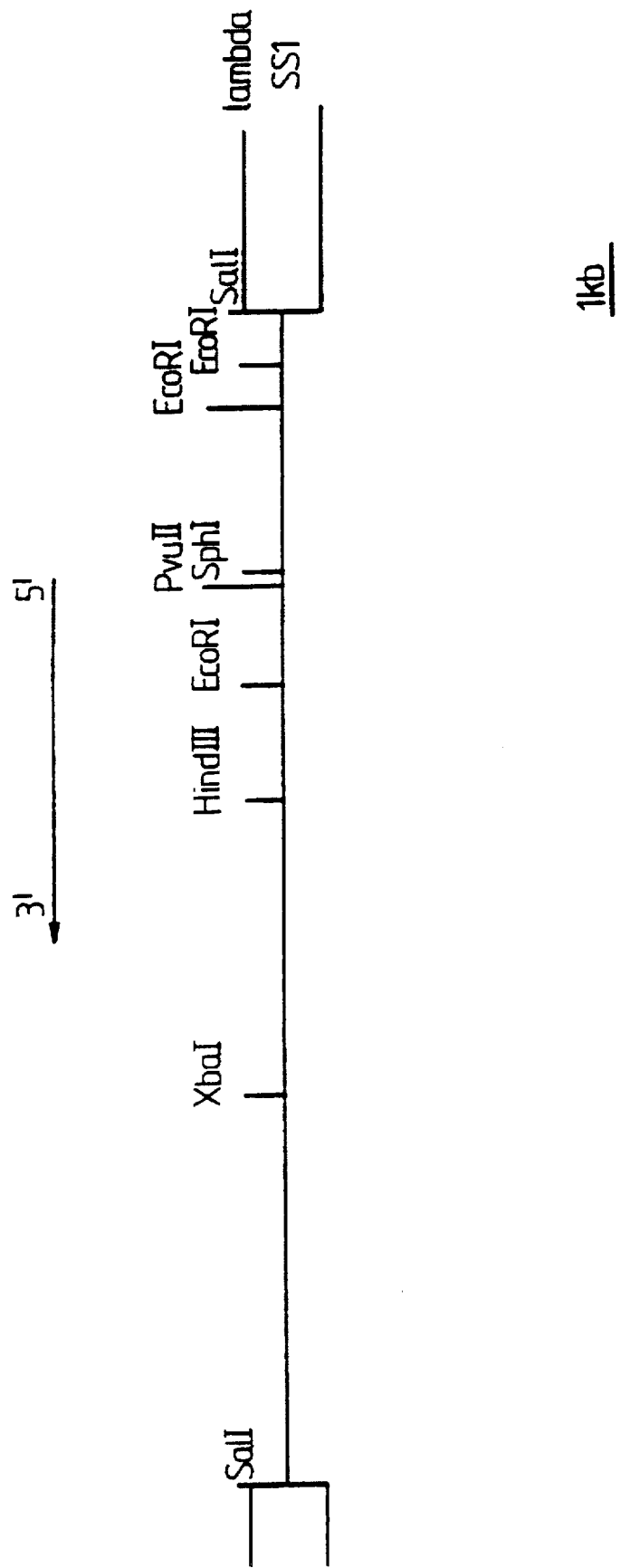
FIG. 1 shows a restriction map of clone lambda SS1, which contains the gene for ovine β-lactoglobulin (BLG)

Characterisation of Recombinant Beta-Lactoglobulin Clones 0.5 µg aliquots of the DNA preparations described above were restricted with a variety of restriction enzymes and the products of the single and double digests analysed by electrophoresis on 0.6% and 1% agarose gels. DNA on these gels was transferred to nitrocellulose filters on to HYBOND membranes (Amersham International, Little Chalfont, Bucks) by the method of Southern (J. Mol. Biol. 98 503 (1975)) and hybridised to $^{32}$P labelled p931. (The word HYBOND is a trademark.) The procedure used was essentially as described above and the hybridised filters were analysed by autoradiography. Using a variety of restriction enzymes and specific probes from the 5' and 3' ends of p931 a restriction map was constructed in which the size and orientation of the β-lactoglobulin gene(s) was determined, (see FIG. 1).

The identity of the β-lactoglobulin clones and the precise position of the 5' and 3' ends of the gene were directly confirmed by DNA sequencing. Using suitable restriction sites, fragments were subcloned into plasmid vectors and into M13 vectors. Sequencing was carried out using the dideoxy method of Sanger et al. (PNAS 74 5463 (1977)).

COMPARATIVE EXAMPLE 2

Expression of the Gene Encoding Ovine Beta Lactoglobulin in Transgenic Mice

Transgenic mice were generated essentially by the techniques described in Gordon and Ruddle, in Methods in Enzymology Vol 101 (1983), (Eds. Wu, Grossman and Moldave), Academic Press pp411–432. Several transgenic mice carrying the 16.2 kb SalI fragment of the clone lambda SS-1 (FIG. 1) were produced. One of these, B-Lac 7, a female was shown to carry 15–20 copies of the SalI fragment. B-lac 7 was mated a number of times and produced a number of offspring which inherited the SS-I sequences.

Milk was obtained from mice 8–12 days after the birth of a litter. This was accomplished by intra-peritoneal injection of 0.31U oxytocin (Sigma) & 7 µl/g animal of Hypnorm/Hypnovel (Fleckneil, Vet. Rec. Dec. 10, 1983, p574), after having previously removed the pups for a four hour period, waiting 20 minutes and then massaging the individual mammary gland by hand. Milk was collected in a 50 µl capillary tube.

Figure 2:
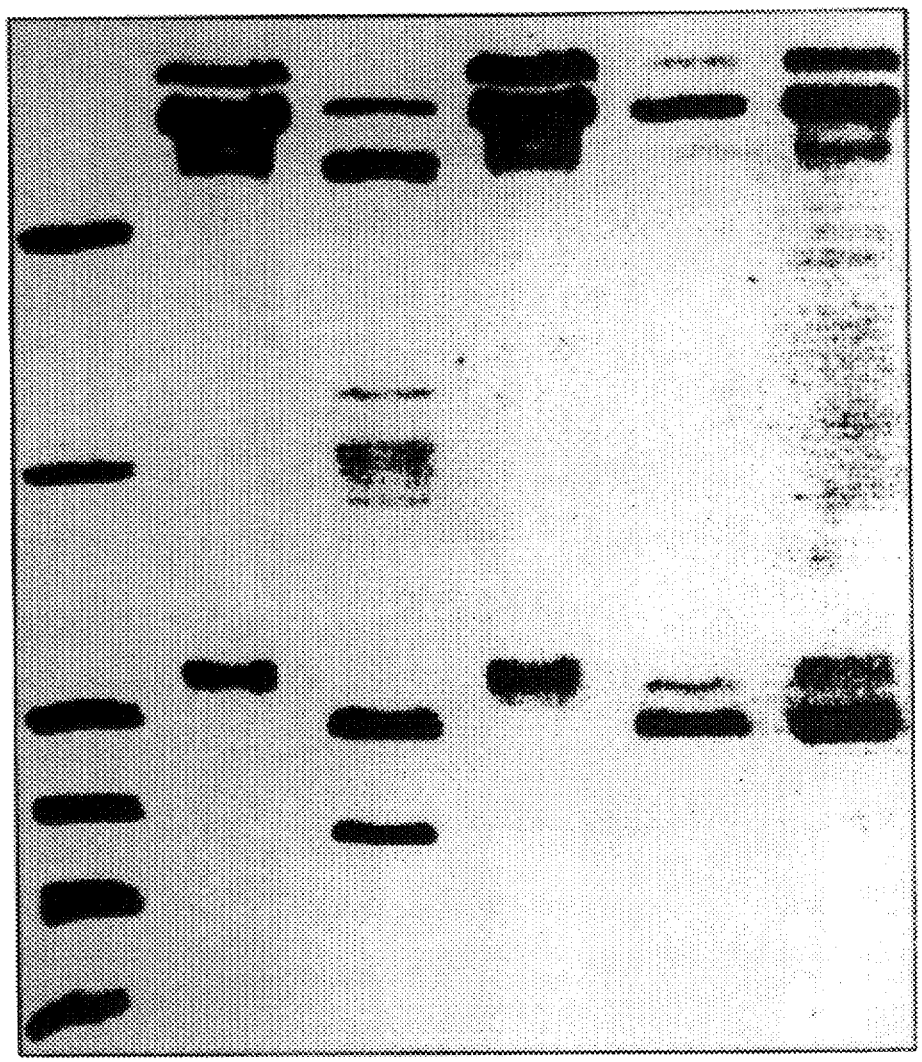
FIG. 2 shows an SDS PAGE analysis of murine and ovine whey proteins (Comparative Example 2)
Figure 3:
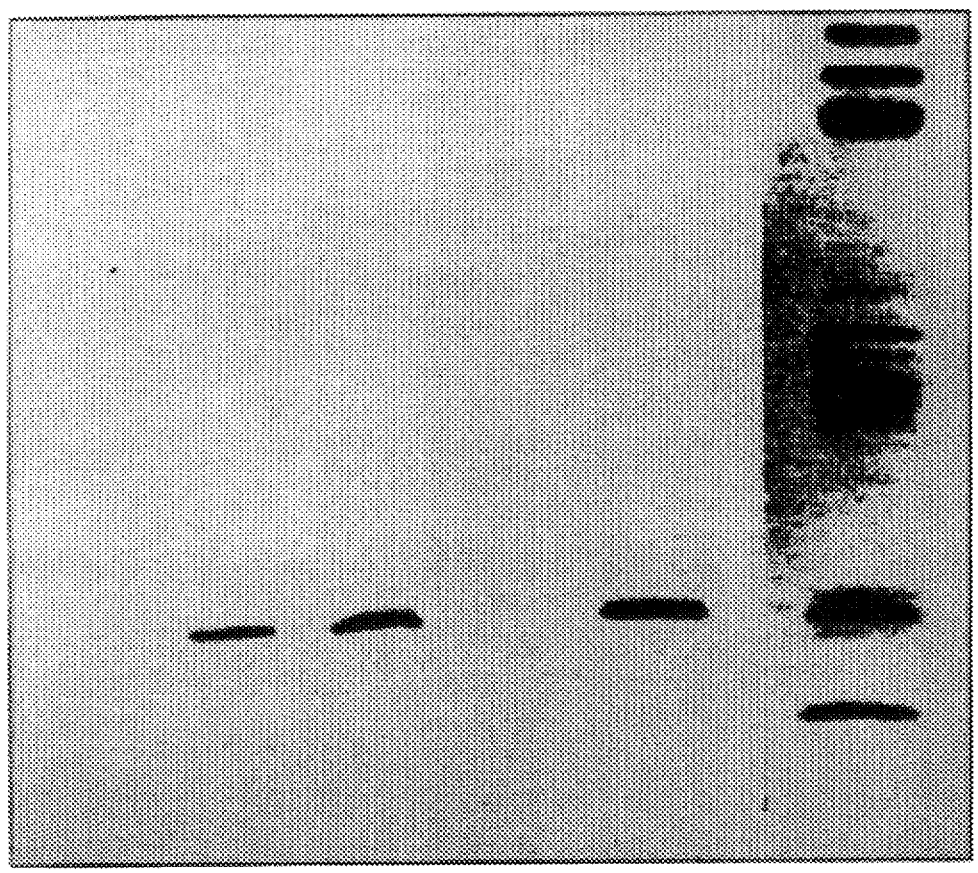
FIG. 3 shows a Western blot of the gel of FIG. 2 using rabbit anti-β-lactoglobulin serum.

The mouse milk was diluted 1:5 in distilled water, centrifuged briefly in a bench centrifuge to defat and the caseins precipitated by addition of 1N HCl to a final pH of 4.6. After centrifugation in a bench centrifuge the whey proteins were removed, precipitated with 5 % trichloracetic acid and analysed by polyacrylamide gel electrophoresis according to Laemmli (Nature 277, 680–684 (1970). FIG. 2 shows an SDS PAGE analysis of murine and ovine whey proteins.) Lane 1, marker proteins; 2, normal mouse whey; 3, sheep whey; 4, normal mouse whey; 5, B-lac7 whey; 6, B-lac7 whey (2.5×5). The band corresponding to β-lactoglobulin in the marker track and in ovine whey is arrowed.) Anti-sera raised in rabbits against ovine β-lactoglobulin was used to detect ovine β-lactoglobulin by Western blotting (Burnett, Anal. Biochem., 112, 195–203, (1981)) on samples resolved by gel electrophoresis. FIG. 3 shows a Western Blot Analysis. The Western blot was reacted with rabbit anti-β-lactoglobulin serum and anti-rabbit Ig peroxidase serum. (Lane 1, marker proteins; 2, sheep whey; 3, B-lac7 whey; 4, normal mouse whey; 5, purified β-lactoglobulin; 6, Coomassie stained sheep whey (run n parallel)).

This analysis showed that large amounts of β-lactoglobulin were secreted into mouse milk, indicating that SS-1 was being expressed at high levels in B-lac 7. This clone presumably contains all the necessary sequences to ensure high levels of expression in the mammary gland of a transgenic mouse and can thus be expected to function as efficiently, if not more so, in the homologous species i.e. in a transgenic sheep. Consequently, fusion genes derived from this clone can also be expected to express (efficiently) in the ovine mammary gland.

COMPARATIVE EXAMPLE 3

The procedure of Comparative Example 2 was followed, except that a 10.5 kb SalI-XbaI fragment from lambda SS-1

(FIGS. 7a and 7b) was used in place of the 16.2 kb SalI fragment (see Simons et al (*Nature* 328 350–532 (1987)). The 10.5 kb fragment derived from lambda SS-1 was cloned into plasmid pPoly1 (see WO-A-8800239 and Lathe et al (*Gene* 57 193–201 (1987) at the XbaI and SalI sites on that plasmid. The resulting plasmid was termed pSS1gXS. High levels of expression were again obtained.

COMPARATIVE EXAMPLE 4

Elaboration of Beta-Lactoglobulin Fusion Genes

Figure 4A:
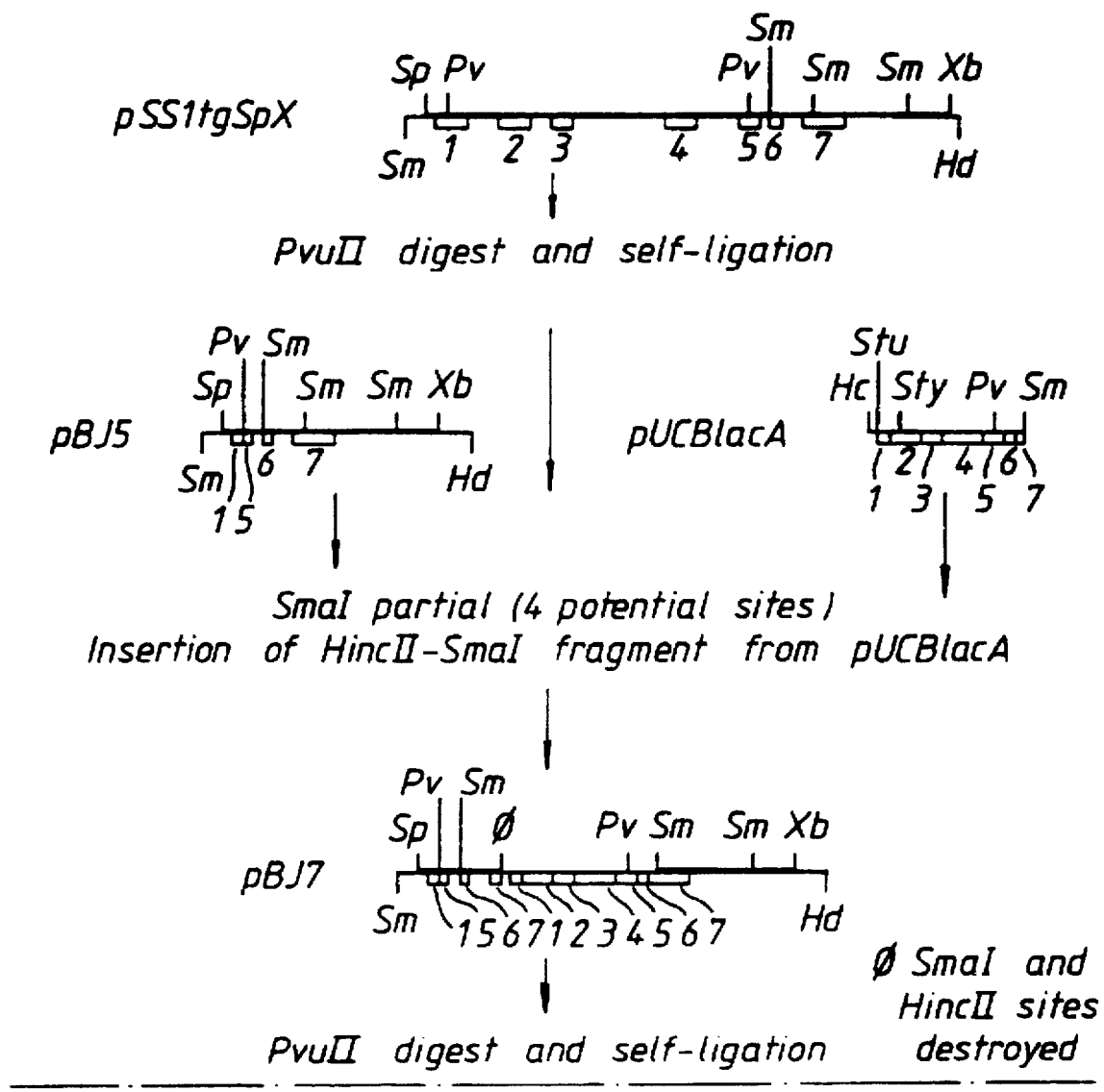
FIGS. 4a and 4b show the construction of plasmid pBJ16 (Comparative Example 4)
Figure 4B:
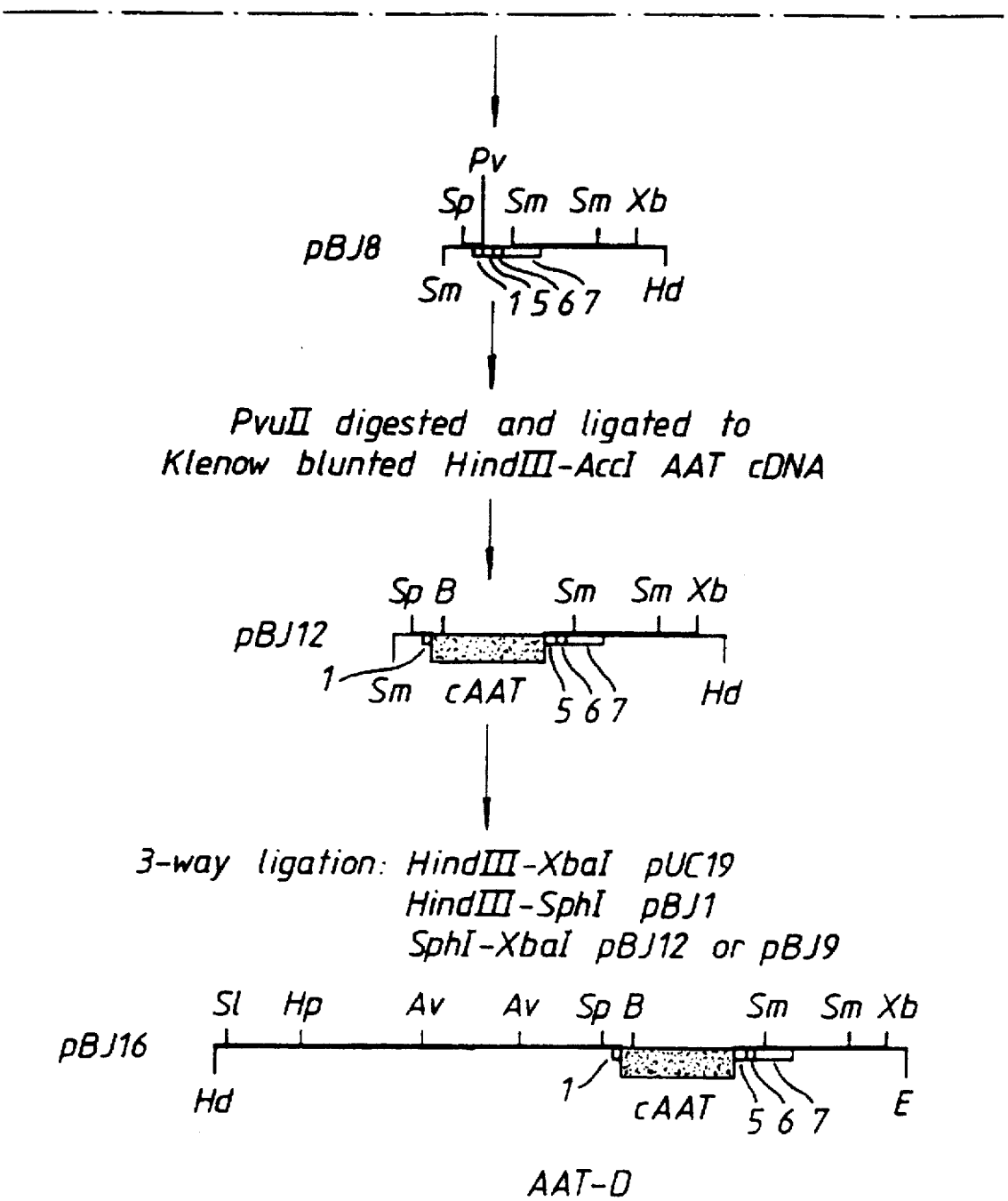

The strategy used for elaborating fusion genes comprising DNA sequence elements from the ovine β-lactoglobulin and DNA coding for $\alpha_1$-antitrypsin to be expressed in the mammary gland is described in this example. FIGS. 4a and 4b summarise the procedure. The approach utilises sequences derived from a lambda clone, lambdaSS-1, which contains the gene for ovine β-lactoglobulin, and whose isolation and characterisation is outlined in WO-A-8800239 (Pharmaceutical Proteins Ltd) and by Ali & Clark (1988) *Journal of Molecular Biology* 199, 415–426.

Specifically, the elaboration of the construct AATD is described. This construct contains the cDNA for human $\alpha_1$-antitrypsin flanked by BLG sequences. The 5' flanking sequences include the SalI to PvuII-0 BLG sequences. The fusion point between the BLG and AAT sequences is in the 5'-untranslated region of the BLG first exon. The 3' flanking sequences comprise exons 6 and 7 of BLG and the 3' flanking sequences of the BLG gene as far as the XbaI site. This construct contains no introns and was designed to examine whether the 5' and 3' BLG sequences described above are sufficient to direct efficient mammary specific expression of cDNAs encoding human plasma proteins as exemplified by that for AAT.

Plasmid pSS1tgSpX

The gel purified SphI-XbaI restriction fragment of about 6.6 kb from pSS1tgXS (described WO-A-8800239) was ligated using T4 DNA ligase to gel purified pPolyI (Lathe, Vilotte & Clark, 1987, *Gene* 57, 193–201) (also described in WO-A-8800239) digested with SphI and XbaI. [The vector pPolyI is freely available from Professor R. Lathe, LGME-CNRS and U184 INSERM, 11 rue Hummann, 67085, Strasbourg, France.] After transformation of competent *E. coli* strain DHRα (Gibco-BRL) the correct clone was identified by restriction enzyme analysis.

Plasmid pBJ5

The gel purified PvuII restrictions fragment containing the origin of replication from pSS1tgSpX was self-ligated using T4 DNA ligase in the presence of 1 mM hexamine cobalt chloride, 25 mM KCI [to encourage self-ligation (Rusche & Howard-Flanders (1985) *Nucleic Acids Research* 13, 1997–2008)]. After transformation of competent *E. coli* strain (Gibco-BRL) the correct clone was identified by restriction enzyme analysis.

Plasmid pUCβlacA

Two complimentary 44-mer oligonucleotides, synthesised by the Oswell DNA Service, Department of Chemistry, University of Edinburgh, and containing bases 117–159 of the ovine β-lactoglobulin cDNA sequence (Gaye et al, (1986) *Biochimie* 68, 1097–1107) were annealed to generate SalI and StyI complimentary termini. The annealed oligo-nucleotides were then ligated using T4 DNA ligase to equimolar amounts of a gel purified 457 bp StyI-SmaI fragment from β-Lg 931 (Gaye et al, op cit) and gel purified pUC19 (Pharmacia-LKB Biotechnology, Pharmacia House, Midsummer Boulevard, Central Milton Keynes, Bucks, MK9 3HP, UK) which had been digested with SalI-SmaI. After transformation of competent *E. coli* strain JM83 (see Messing (1979) Recombination DNA Technical Bulletin, NIH Publication No. 79–99, 2, No. 2 (1979), 43–48) the correct recombinant was determined by restriction analysis.

Plasmid pBJ7

The gel purified HincII-SmaI restriction fragment from pUCβlacA was ligated using T4 DNA ligase to gel purified pBJ5 linearised by partial digestion with SmaI. After transformation of competent *E. coli* strain DH5α (Gibco-BLR) the correct clone was identified by restriction enzyme analysis.

Plasmid pBJ8

The gel purified PvuII restriction fragment containing the origin of replication from pBJ7 was self-ligated using T4 DNA ligase in the presence of 1 mM hexamine cobalt chloride, 25 mM KCI (to encourage self-ligation [Rusche & Howard-Flanders (1985) *Nucleic Acids Research* 13, 1997–2008)]. After transformation into competent *E. coli* strain DH5α (Gibco-BRL) the correct clone was identified by restriction enzyme analysis.

Plasmid pUC8α1AT.73

The plasmid p8α1ppg containing a full-length cDNA encoding an M variant of $\alpha_1$-antitrypsin was procured from Professor Riccardo Cortese, European Molecular Biology Laboratory, Meyerhofstrasse 1, D-6900 Heidelberg, Federal Republic of Germany (Ciliberto, Dente & Cortese (1985) *Cell* 41, 531–540). The strategy used in the contrast BLG-AAT or pSS1tgXSTARG, now known as AATA, described in WO-A-8800239 required that the polyadenylation signal sequence at the 3' end of the $\alpha_1$-antitrypsin cDNA be removed.

The polyadenylation signal was removed in the following manner. Plasmid p8α1ppg DNA was digested with PstI and the digestion products were separated by electrophoresis in a preparative 1% agarose gel containing 0.5 μg/ml ethidium bromide (Sigma). The relevant fragment of about 1400 bp was located by illumination with a UV lamp (Ultra-Violet Products, Inc, San Gabriel, Calif., U.S.A.). A piece of dialysis membrane was inserted in front of the band and the DNA fragment subsequently electrophoresed onto the membrane. The DNA was eluted from the dialysis membrane and isolated by use of an 'ElutipD' [Scleicher and Schull, Postfach 4, D-3354, Dassel, W. Germany], employing the procedure recommended by the manufacturer. The gel purified 1400 bp PstI fragment was digested with the TaqI, electrophoresed on a preparative 1% agarose gel as described above. The TaqI-PstI fragment of approximately 300 bp comprising the 3' end of the $\alpha_1$-antitrypsin cDNA including the polyadenylation signal sequence was eluted and purified using an Elutip as described above, as was the TaqI-TaqI fragment of 1093 bp containing the 5' portion of the cDNA. The plasmid vector pUC8 (Pharmacia-LKB Biotechnology, Pharmacia House, Midsummer Boulevard, Central Milton Keynes, Bucks, MK9 3HP, UK) was digested with AccI and PstI, phenol/chloroform extracted and DNA recovered by ethanol precipitation. The 300 bp TaqI-PstI fragment from p8α1ppg was ligated using T4 DNA ligase to pUC8 cut with AccI and PstI and the ligation products were used to transform *E. coli* strain DH-1 (Gibco-BRL, PO Box 35, Trident House, Renfrew Road, Paisley PA3 4EF, Scotland UK) to ampicillin resistance. Plasmid DNA was isolated from ampicillin resistant colonies. The correct recombinants were identified by the release of a fragment of approximately 300 bp on double digestion with AccI and PstI. The plasmid generated was called pUC8.3'AT.3.

Plasmid pUC8.3'AT.3 was subjected to partial digestion with BstNI and the fragment(s) corresponding to linearised pUC8.3'AT.3 isolated from an agarose gel. There are seven BstNI sites in pUC.3'AT.3, five in the vector and two in the region corresponding to the 3'-untranslated sequences of $\alpha_1$-antitrypsin. The BstNI linearised with gel purified DNA was digested with PstI which cuts in the pUC8 polylinker where it joins the 3' end of the cDNA insert. The PstI digested DNA was end repaired with T4 DNA polymerase in the presence of excess dNTPs and self-ligated with T4 DNA ligase. The BstNI-PstI fragment containing the polyadenylation signal sequence is lost by this procedure. The ligated material was used to transform *E. coli* DH-1 to ampicillin resistance. Plasmid DNA was isolated from ampicillin resistant colonies. The correct clone was identified by restriction analysis and comparison with pUC8.3'AT.3. The correct clone was characterised by retention of single sites for BamHI and HindIII, loss of a PstI site, and a reduction in the size of the small PvuII fragment. The correct clone was termed pB5.

Plasmid pB5 DNA was digested with AccI, phenol/chloroform extracted and DNA recovered by ethanol precipitation. AccI cleaved pB5 DNA was treated with calf intestine alkaline phosphatase (BCL). The reaction was stopped by adding EDTA to 10 millimolar and heating at 65° C. for 10 minutes. The DNA was recovered after two phenol/chloroform and one chloroform extractions by precipitation with ethanol. T4 DNA ligase was used to ligate the 1093 bp TaqI-TaqI fragment described above to pB5, AccI cleaved and phosphatased DNA and the ligation products were used to transform *E. coli* strain HB101 (Gibco-BRL) to ampicillin resistance. The identity of the correct clone (pUC8∝1AT.73) was verified by restriction analysis— presence of a 909 bp HinfI fragment, a 1093 bp TaqI fragment, and a 87 bp BamHI fragment.

Plasmid pBJ12

Plasmid pUC8α1AT.73 was digested with AccI and HindIII and the resulting fragment containing the $\alpha_1$-antitrypsin cDNA minus its polyadenylation signal was end-repairing using Klenow fragment of *E. coli* DNA polymerase in the presence of excess dNTPs. This blunt ended fragment was gel purified and ligated using T4 DNA ligase to gel purified pBJ8 linearised with PvuII. After transformation of competent *E. coli* strain DH5α (Gibco-BRL) the correct clone was identified by restriction enzyme analysis.

Plasmid pSS1tgSpS

The gel purified SalI-SphI restriction fragment of approximately 4.2 kb isolated from pSS1tgXS (described in WO-A-8800239) was ligated, using T4 DNA ligase, with equimolar amounts of gel purified pPolyI (Lathe, Vilotte & Clark, 1987, *Gene* 57, 193–201) digested with SalI and SphI. [The vector pPolyI is freely available from Professor R. Lathe. LGME-CNRS and U184 INSERM, 11 rue Humann, 67085 Strasbourg, France.] After transformation of competent *E. coli* strain DH1 (Gibco-BRL) the correct clone was identified by restriction analysis.

Plasmid pBJ1

Plasmid pSS1tgSpS was digested with BglII and end-repaired using the Klenow fragment of *E. coli* DNA polymerase in the presence of excess dNTPs. The blunt-ends were modified using HindIII synthetic linkers (New England Biolabs Inc, 32 Tozer Road, Beverly, Mass. 01915-5510, U.S.A.) and the resulting fragment self-ligated using T4 DNA ligase in the presence of 1 mM hexamine cobalt chloride, 25 mM KCI (to encourage self-ligation [Rusche & Howard-Flanders (1985) *Nucleic Acids Research* 13, 1997–2008)]. After transformation of competent *E. coli* strain DH5α (Gibco-BRL) the correct clone was identified by restriction enzyme analysis.

Plasmid pBJ16 (AATD)

The gel purified HindIII-SphI fragment from pBJ1 and the gel purified SphI-XbaI fragment from pBJ12 were ligated using T4 DNA ligase to gel purified pUC19 (Pharmacia-LKB Biotechnology, Pharmacia House, Midsummer Boulevard, Central Milton Keynes, Bucks, MK9 3HP, UK) digested with HindIII and XbaI. After transformation of competent *E. coli* strain DH5α (Gibco-BRL) the correct clone was identified by restriction enzyme analysis.

Isolation of AAT-D Fragment from pBJ15 for Microinjection

Plasmid pBJ16 was digested with HindIII and XbaI and the resulting 8.0 kb AATD fragment was isolated from a gel using DE81 paper (Dretzen et al (1981) *Analytical Biochemistry* 112, 285–298). After separation from the DE81 paper the DNA was phenol/chloroform extracted, ethanol precipitated and finally resuspended in TE buffer (10 mM Tris-HCl, 1 mM EDTA pH 8) ready for microinjection.

COMPARATIVE EXAMPLE 5

The AATD construct described in Comparative Example 4 above was used to generate transgenic mice by the method described in Example 1 of WO-A-9005188. RNA isolated from various tissues was examined for the presence of AATD transcripts and milk from the females was assayed for the presence of $\alpha_1$-antitrypsin by Western blotting; both of these analyses are as described in Example 2 of WO-A-9005188. The results are shown in Table 1 below:

TABLE 1

| Mice | Description | RNA | AAT Protein* |
|---|---|---|---|
| AATD12 | GO female | — | — |
| AATD14 | GO female | — | — |
| AATD31 | GO female | — | — |
| AATD33 | GO female | — | 3.9 µg/ml |
| AATD9 | mouse-line | — | — |
| AAT21 | mouse-line | — | — |
| AATD41 | mouse-line | — | — |
| AATD47 | mouse-line | — | — |

*assessed by Western blotting and/or ELISA

Only ⅛ of the transgenic mice carrying AATD expressed the transgene as determined by analysis of milk proteins. The level of expression was quite low and despite repeated attempts no corresponding AATD RNA transcripts were detected in the mammary gland.

EXAMPLE 1

The β-lactoglobulin construct prepared in Comparative Examples 1 and 3, containing the 10.5 kb SalI-XbaI fragment prepared from pSS1gXS ("BLG") and the $\alpha_1$-antitrypsin construct prepared in Comparative Example 3 ("AATD") were co-injected into mouse eggs as before in an equimolar ratio in a total DNA concentration of about 3 µg/ml. 20 transgenic founder mice were detected by Southern blotting and 11 of these were found to carry both AATD and BLG sequences. These mice were designed BAD (BLG and AATD). 9/11 transmitted both transgenes to the G1 progeny. Analysing a number of progeny in each line showed that in each case the two transgenes had segregated together (FIGS. 5a and 5b) indicating that they were integrated very close together and in all probability were co-integrated at the same site.

Figure 5A:
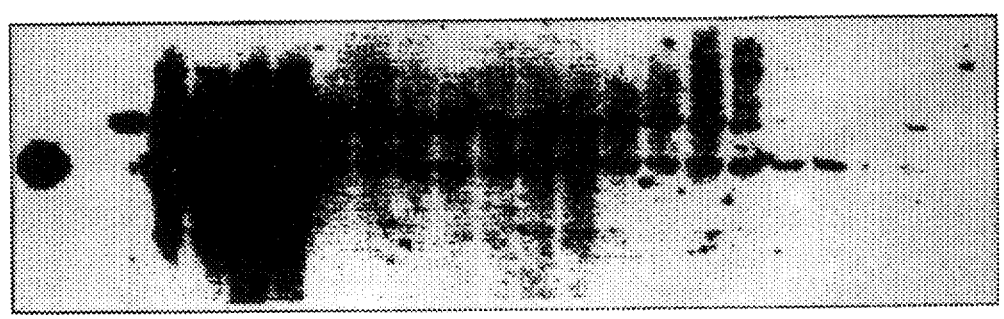
FIGS. 5a and 5b show Southern blots from mice resulting from co-injection of BLG and AATD and indicate the co-segregation of the two transgenes (Example 1); Band 1 is a BLG-specific band; and Band 2 is an AATD-specific band.
Figure 5B:
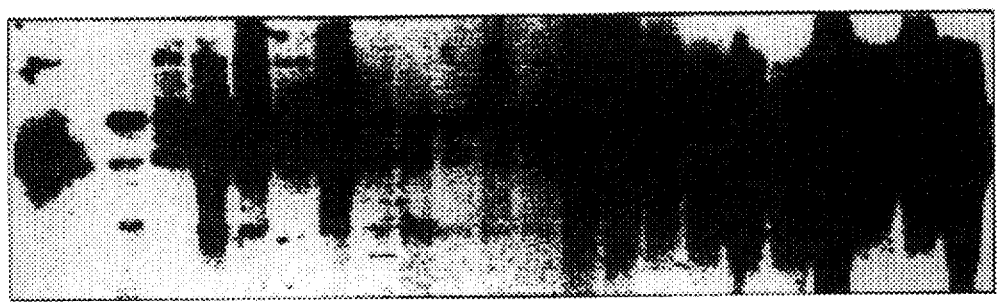

FIGS. 5a and 5b show the co-segregation of AATD and BLG. DNA samples from the various BAD lines resulting from co-injection with AATD and BLG were restricted with EcoRI, Southern blotted and probed with an EcoRI-SphI fragment that hybridised to the 5' end of the two transgenes. BLG and AATD transgenes can be distinguished by EcoRI digestion and the specific EcoRI fragments are indicated. DNA from a number of G1 animals has been analysed. The similar pattern of AATD and BLG restriction fragments in G1 animals from the sane line (i.e. BAD 1; BAD99 etc) is indicative of co-segregation. Note that line BAD93 may have two co-integrated loci which are segregating in the G1 generation.

Expression of AATD mRNA has been analysed in all of the 9 lines of the double transgenic mice. AATD transcripts of the expected size were detected in mammary RNA in 6 out of the 9 lines: 3 lines expressed AATD mRNA at low levels, 1 at medium level and 2 at high level. AATD transcripts were not detected in other tissues (FIG. 6).

Figure 6:
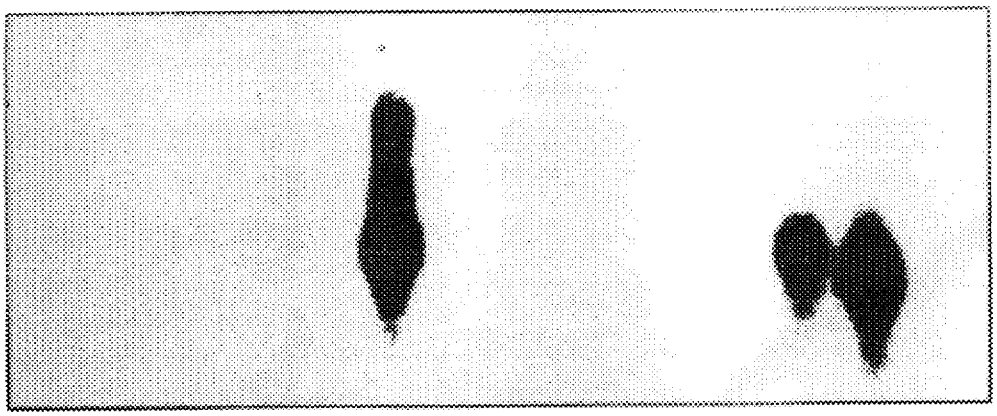
FIG. 6 shows a Northern blot showing the result of hybridisation experiments indicating the tissue specific expression of an AATD transgene in mice according to the invention (Example 1)

FIG. 6 shows tissue-specific expression of AATD in BAD lines. RNA prepared from a variety of tissues was probed with human AAT-specific sequences. The ~1600 nt AATD transcripts (arrowed D) are seen specifically in the mammary gland of BAD mice 99.3 and BAD 135.13. The ~1400 nt transcripts from transgene AATB (arrowed B) expressed in the mammary gland) in transgenic line AATB 35 (35M); CM, control mouse mammary gland RNA (see also Example 2 of WO-A-9005188). Sa; salivary gland; H, heart; K, kidney; Sp, spleen; L, liver; M, Mammary gland.

Human $\alpha_1$-antitrypsin has been measured in the two high expressing lines and estimated at about 140 µg/ml and about 600 µg/ml (mean values of two) respectively. The BLG transgene has also been analysed for expression: the 6 lines that expressed AATD mRNA also expressed BLG mRNA, whereas the three AATD lines apparently negative for AATD mRNA do no apparently express BLG (representative example shown in FIGS. 7a and 7b). FIGS. 7a and 7b illustrate direction of AATD and BLG transcripts in BAD mice. Mammary gland (M) and liver (L) RNA samples, blotted onto Hybond membranes, were probed with AAT ($\alpha$1AT). ~1600 nt AATD transcripts are detectable in mammary gland RNA samples from BAD mice 1.1, 1.2, 36.8, 107.2, 158.3, 99, 99.3 and 135.13. The filters were stripped and re-hybridised to a BLG-specific probe (BLG); the same samples showed strong hybridisation to the ~800 nt BLG transcript; also detected in sheep mammary gland RNA (SM); AATB 35, mammary gland RNA from transgenic line AATB 35 containing ~1400 nt AATB transcript; CM, control mouse samples.

It therefore appears that at least for the most part AATD expression may be associated with an actively expressing BLG gene. Comparing the results of this example with those of Comparative Example 5, it appears that the co-injection (and presumably co-integration) of AATD with BLG has significantly increased the efficiency of AATD. Considering RNA data only, when AATD was injected alone 0/8 animals expressed the transgene. When co-injected (and presumable co-integrated) with BLG, expression of AATD mRNA was detected in 6/9 animals as shown in Table 2 below.

TABLE 2

| Mouse/ | RNA[1] | | Protein | |
|---|---|---|---|---|
| | | | $\alpha$1AT[2] | BLG[3] |
| Line | $\alpha$1AT | BLG | (µg/ml) | (mg/ml) |
| BAD 1 | + | + | 4.8 | 9 |
| BAD 36 | + | − | 1.2 | 1.1 |
| BAD 41 | − | − | — | — |

TABLE 2-continued

| Mouse/ | RNA[1] | | Protein | |
|---|---|---|---|---|
| | | | $\alpha$1AT[2] | BLG[3] |
| Line | $\alpha$1AT | BLG | (µg/ml) | (mg/ml) |
| BAD 93 | − | − | (.84)[4] | — |
| BAD 99 | + | + | 137 | 1.7 |
| BAD 107 | + | + | 24 | 2.4 |
| BAD 135 | + | + | 610 | 1.7 |
| BAD 144 | − | − | — | — |
| BAD 158 | + | + | 1 | 1.6 |

Expression in BAD Transgenic Mice
[1]mRNA transcripts detected on N. blots of total and poly A + RNA.
[2]$\alpha$1AT determined by ELISA: sensitivity > 0.2 µg/ml. For BAD lines values represent average from 2 mice.
[3]BLG estimated densitometrically on SDS-PAGE gels by reference to BLG standard.
[4]Expression detected in only one out of two animals from this line.

COMPARATIVE EXAMPLE 6

The procedure of Example 4 (construction of AATD) is repeated, except that the DNA sequence encoding the polypeptide of interest encodes Factor IX. A NheI-HindIII fragment comprising 1553 bp of the insert from p5'G3'CV1 [see WO-A-8800239] was inserted into the PvuII site of pBJ8 as described above for pBJ12 to generate FIX D.

COMPARATIVE EXAMPLE 7

The FIX construct described in Comparative Example 6 above was used to generate transgenic mice by the method described in Example 1 of WO-A-9005188. RNA isolated from various tissues was examined for the presence of FIX transcripts and milk from the females was assayed for the presence of factor IX by Western blotting and/or ELISA; both of these analyses are as described in Example 2 of WO-A-9005188. The results are shown in Table 3 below:

TABLE 3

| Mice | Description | RNA | FIX Protein* |
|---|---|---|---|
| FIX D 11 | G0 female | — | — |
| FIX D 14 | G0 female | — | — |
| FIX D 16 | G0 female | — | — |
| FIX D 17 | G0 female | — | — |
| FIX D 18 | G0 female | — | — |
| FIX D 20 | mouse-line | — | — |
| FIX D 23 | mouse-line | — | — |
| FIX D 24 | mouse-line | — | — |
| FIX D 26 | mouse-line | — | — |

*assessed by Western blotting and/or ELISA

None of the transgenic mice carrying FIX D expressed the transgene as determined by analysis of milk proteins or by Northern blotting of mammary gland RNA.

EXAMPLE 2

The β-lactoglobulin construct prepared in Comparative Examples 1 and 3, containing the 10.5 kb SalI-XbaI fragment prepared from pSS1tgXS ("BLG") and the factor IX construct prepared in Comparative Example 3 ("FIX D"), were co-injected into mouse eggs as before but in a molar ratio of 3 BLG:1 FIX D in a total DNA concentration of about 3 µg/ml. 30 transgenic founder mice were detected by Southern blotting and 20 of these were found to carry both FIX and BLG sequences. These mice were designated BIX (BLG and FIX D). 12/13 transmitted both transgenes to the G1 progeny. Analysing a number of progeny in each line showed that in each case the two transgenes had segregated together (FIG. 8) indicating that they were integrated very close together and in all probability were co-integrated at the same site.

FIG. 8 shows the co-segregation of FIX D and BLG. DNA samples from the various BIX lines resulting from co-injection with FIX D and BLG were restricted with BamHI, Southern blotted and probed with an EcoRI-SphI fragment that hybridised to the 5' end of the two transgenes. BLG and FIX D transgenes can be distinguished by BamHI digestion and the specific BamHI fragments are indicated. DNA from a number of G1 animals has been analysed. The similar pattern of FIX D and BLG restriction fragments in G1 animals from the same line (e.g. BIX 34; BIX 99 etc) is indicative of co-segregation. Note that line BIX 29 may have two co-integrated loci which are segregating in the G1 generation.

Expression of FIXD mRNA has been analysed in 11 of the 12 lines of the double transgenic mice. The FIX D transcripts of the expected size were detected in mammary RNA in all these lines: 4 lines expressed FIX mRNA at low levels, 4 at medium level and 3 at high level. (Some variation in the level of expression between individual mice of a given line was observed in some cases.) FIX D transcripts were not detected in other tissues (FIG. 9).

FIG. 9 shows tissue-specific expression of FIX D in BIX lines. RNA prepared from a variety of tissues was probed with fIX-specific sequences. The ~1800 nt FIX D transcripts (arrowed) are seen specifically in the mammary gland of BIX mice 12.1, 30.2 and 33.1. The ~2600 nt transcript from the endogenous FIX gene (arrowed B) is present in liver samples. CM, control mouse mammary gland RNA (see also Example 2 of WO-A-9005188) CL, control liver RNA. Sa; salivary gland; H, heart; K, kidney; Sp, spleen; L, liver; M, mammary gland. FIX A51, mammary gland RNA from a transgenic mouse carrying a second FIX transgene, FIX A that expresses a ~240 nt FIX transcript (arrowed A). Human factor IX was detected in the milk from mice from 6 out of the 10 lines which have been analysed—see Table 4 below. The BLG transgene has also been analysed for expression; all the lines analysed were shown to express BLG mRNA also expressed BLG mRNA.

FIGS. 10a and 10b illustrate detection of FIX D and BLG transcripts in BIX mice. Mammary gland (M) an liver (L) RNA samples, blotted onto Hybond membranes, were probed with fIX specific sequences. ~1800 nt FIX D transcripts are detectable in mammary gland RNA samples from BIX mice 34.1, 37.1, 43.3, 66.2, 10.3, 12.1, 30.4, 33.1, 22.13, 29 and 131.2. The filters were stripped and re-hybridised to a BLG-specific probe (BLG); the same samples showed hybridisation to the ~800 nt BLG transcript, FIX A 51, mammary gland RNA from transgenic mouse FIX A 51 containing ~2400 nt FIX A transcript; C, control mouse samples.

Comparing the results of this example with those of Comparative Example 6, it appears that the co-injection (and presumably co-integration) of FIX D with BLG has significantly increased the efficiency of expression of FIX D. Considering RNA data only, when FIX D was injected alone, 0/9 mice lines expressed the transgene. When injected (and presumably co-integrated) with BLG, expression of FIX D mRNA was detected in 11/11 lines as shown in Table 4 and FIX proteins detected in the milk of a further line for which RNA was not available.

TABLE 4

| Mouse/ | Expression in BIX transgenic mice BIX | | | |
|---|---|---|---|---|
| | RNA[1] | | Protein | |
| Line | fIX | BLG | fIX[2] | BLG[3] |
| 10 | + | + | − | + |
| 12 | + | + | + | + |
| 22 | + | + | − | + |
| 29 | + | + | + | + |
| 30 | + | + | + | + |
| 32 | n.d. | n.d. | + | + |
| 33 | + | + | + | + |
| 34 | + | + | − | + |
| 37 | + | + | n.d. | + |
| 43 | + | + | n.d. | + |
| 66 | + | + | − | + |
| 131 | + | + | + | + |

Notes:
[1]mRNA transcripts detected on N blots of total mammary gland RNA
[2]fIX detected by W blotting and/or ELISA
[3]BLG detected on Coomassie blue stained SDS-PAGE gels.
n.d. not done.

EXAMPLE 3

A β-lactoglobulin/bovine α-lactalbumin construct (BLG/alacTR.D—BAT) was prepared in the following way. The 3.0 XhoI fragment comprising regulatory sequences derived from the bovine α-lactalbumin gene fused to a segment of DNA encoding ovine trophoblastin was excised from the plasmid vector (for full details of this plasmid construct see Stinnakre et al (1991), FEBS Letters, 284 1, 19–22). This fragment was inserted directly into the plasmid pS1tgXS (see WO-A-8800239) at the unique SalI site (FIG. 11). The resulting 13.5 kb insert comprising the alacTR gene linked to the BLG gene was excised from the plasmid vector by digestion with XbaI. This fragment was purified by gel electrophoresis and used for the direct microinjection of mouse eggs, as previously described.

EXAMPLE 4

All references to the DNA sequence of the β-lactoglobulin gene utilise the numbering of the sequence allocated EMBL Accession No. X12817 (Harris et al, NAR 16:10379–80 (1988)).

Plasmid pUC.PM

The multiple cloning site of the vector pUC18 (Yanisch-Perron et al, (1985) Gene 33:103–119) was removed and replaced with a synthetic, double stranded, oligonucleotide containing the new restriction sites: PvuI/MluI/SalI/EcoRV/XbaI/PvuI/MluI, and flanked by 5'-overhangs compatible with the restriction sites EcoRI and HindIII. pUC18 DNA was cleaved with both EcoRI and HindIII, the 5'-terminal phosphate groups were removed with Calf Intestinal Phosphatase to prevent religation of this starting material. The new linker DNA was ligated into pUC18. The DNA sequence across the new multiple cloning site was confirmed. This new vector was called pUC.PM.

Plasmid pUCXS

The β-lactoglobulin gene sequences from the plasmid pSS1tgXS (see Comparative Example 3 above) were excised on a SalI and XbaI fragment and recloned into the vector pUC.PM, cut with SalI and XbaI, to give plasmid pUCXS.

Plasmid pUCXC/RV

The plasmid pSS1tgSE (see WO-A-8800239) contains β-lactoglobulin gene sequences from the SphI size at position 754 to the EcoRI site at 2050, a region spanning a unique NotI site at position 1148. This inset contains a single PvuII site (832) which lies in the 5'-untranslated of the β-lactoglobulin mRNA. Into this site was blunt-end ligated a double stranded, 8 bp, DNA liner encoding the recognition site for the enzyme EcoRV, to give the plasmid pSS1tgSE/RV. The DNA sequences bounded by SphI and NotI were then excised and used to replace the equivalent fragment in the plasmid pUCXS, thus effectively introducing a unique EcoRV site into the β-lactoglobulin gene placed in such a way as to allow the insertion of any additional DNA sequences under the control of the β-lactoglobulin gene promotor and 3' to the initiation of transcription. The resulting plasmid was called pUCXS/RV.

Plasmid pUCSV

A derivative of pUCXS/RV, containing only the 4.2 kbp of the β-lactoglobulin gene which lie 5' to the transcription initiation site (the promoter), was constructed by subcloning the SalI-EcoRV fragment into pUC.PM; this plasmid is called pUCSV.

Plasmid pBLAC100

A fragment of the 3' flanking sequence of the β-lactoglobulin gene were subcloned in such a way as to eliminate all introns. Plasmid DNA of pUCSX/RV which was partially digested with SmaI by performing an enzyme titration with lower and lower concentrations of enzyme at a fixed concentration of DNA. The SmaI protein was removed by phenol-chloroform extraction and ethanol precipitation and the DNA resuspended in water. This DNA was subsequently digested to completion with the enzyme XbaI. DNA cut once at the SmaI site, position 5286, and then cleaved with XbaI gave a characteristic band of size 2.1 kbp. This band was purified from an agarose gel slice and ligated into SmaI and XbaI cut pBSIISK+ (Stratagene Ltd, Cambridge Science Park, Cambridge, UK) to give the plasmid pBLAC100.

Plasmid pMAD

The β-lactoglobulin cloning vector pMAD was constructed to allow rapid insertion of cDNAs under the control of the β-lactoglobulin gene promoter and 3'-flanking sequences. Such constructs contain no introns. The plasmid pBLAC100 was opened by digestion with both EcoRV and SalI, the vector fragment was gel purified. Into this was ligated the 4.2 kbp promoter fragment from the plasmid pUCSV as a SalI-EcoRV fragment. This construct is termed pST1 and constitutes a β-lactoglobulin mini-gene encoding the 4.2 kbp promoter and 21 kbp of 3'-flanking sequences. A unique EcoRV site is present to allow blunt-end cloning of any additional DNA sequences. In order to allow excision of novel β-lactoglobulin gene constructs with the enzyme MluI the entire mini-gene from pST1 was excised on a XhoI-NotI fragment, the DNA termini made flush with Klenow polymerase, under standard conditions, and blunt-end cloned into the EcoRV site of pUC.PM to give pMAD.

Plasmid pCORP2

A 1450 bp cDNA of the protein C gene, flanked by KpnI sites, was obtained in the form of plasmid pWAPC2. The cDNA was excised as a KpnI fragment, the 3' overhangs made flush by treatment with T4 DNA polymerase, the fragment gel purified and blunt-end cloned into the EcoRV site of pMAD. Orientation was determined by restriction digest and confirmed by DNA sequencing. This construct is plasmid pCORP2 and contains the protein C cDNA under the transcriptional control of the β-lactoglobulin gene 5' and 3' flanking sequences. There are no introns.

Isolation of CORP2 fragment from pCORP2 for Microinjection

Plasmid pCORP2 was digested to completion with MluI and the resulting 7.75 kbp CORP2 fragment was excised from a 1% agarose gel after electrophoretic separation. The DNA was purified from the agarose slice using the PREP-AGENE® kit (Biorad) and eluted in TE buffer ready for dilution and microinjection.

Transgenic Mouse Production

Transgenic mice were generated by direct pro-nuclear injection essentially as described by Gordon and Ruddle, "Methods in Enzymology", Vol 101, [(1983) Eds. Wu, Grossman and Moldave], Academic Press pp 411-432. The 'β-Lactoglobulin' construct and the 'Protein C' construct were co-injected at both equimolar ratio and non-equimolar ratio (1:3 with respect to Protein C) at an overall concentration of 6 µg/ml. 12 founder mice were produced, all of which had integrated both transgenes.

Injection of CORP2 DNA alone into the mouse eggs resulted in the generation of 11 lines of transgenic mice. Milk was collected from these mice and analysed for the presence of Protein C by ELISA. The ELISA was based on the double antibody sandwich principle and used rabbit polyclonal antibodies raised against human plasma derived Protein C. The ELISA is capable of measuring Protein C levels as low as 100 ng/ml but was unable to detect Protein C in any of the 11 lines of transgenic CORP2 mouse milks (see Table 5).

TABLE 5

Levels of human protein C in the milk of transgenic mice containing the CORP 2 construction alone.

| Mouse Line | Protein C Concentration |
| --- | --- |
| 94-15 | -ve |
| 94-13 | -ve |
| 94-4 | -ve |
| 94-9 | -ve |
| 95-3 | -ve |
| 97-4 | -ve |
| 96-28 | -ve |
| 95-10 | -ve |
| 96-26 | -ve |
| 97-15 | -ve |
| 97-22 | -ve |

Co-injection of the CORP 2 construct with the ovine β-lactoglobulin gene (UCXS/RV) resulted in the generation of three transgenic lines. Table 6 shows the levels of Protein C in milk sample taken from these mice as measured by the ELISA described above.

TABLE 6

Levels of human Protein C in the milk of transgenic mice containing both the CORP 2 construct and ovine β-lactoglobulin gene (UCXS/RV).

| Mouse Line | Protein C Concentration |
| --- | --- |
| 99-2 | 1.7 µg/ml |
| 102-7 | 15 µg/ml |
| 103-4 | -ve |

I claim:

1. A method for enhanced production of a protein of interest which comprises:
   (a) producing milk in a female transgenic, non-human mammal whose somatic and germ cells contain:
      (i) a first transgene construct comprising a DNA sequence encoding said protein of interest operatively linked to a mammary gland specific promoter, and (ii) a second transgene construct comprising a regulatory sequence from a mammary gland specific gene, said transgene construct having been co-introduced into said mammal or an ancestor of said mammal at an embryonic stage, wherein said protein of interest is expressed in the mammary gland and secreted into the milk of said mammal, and wherein said expression is at a higher level than when said first transgene construct is introduced in the absence of said second transgene construct; and (b) collecting the milk produced in step (a) and isolating said protein of interest.

2. A method as in claim 1, wherein the DNA sequence encoding said protein is cDNA.

3. A method as in claim 1, wherein the DNA sequence encoding said protein is isolated from a milk protein gene.

4. A method as in claim 3, wherein the DNA sequence encoding said protein is isolated from the same gene sequence as the regulatory sequence.

5. A method as in claim 3, wherein the regulatory sequence is from a mammary gland specific gene isolated from the same species as the trangenic mammal.

6. A method as in claim 1, wherein the protein has pharmaceutical activity.

7. A method for enhanced production of a protein of interest which comprises:

(a) producing milk in a female transgenic, non-human mammal whose somatic and germ cells contain a transgene construct comprising:

(i) a first DNA sequence encoding said protein of interest operatively linked to a mammary gland specific promoter, and (ii) a second DNA sequence comprising a regulatory sequence from a mammary gland specific gene, said transgene construct having been introduced into said mammal or an ancestor of said mammal at an embryonic stage, wherein said protein of interest is expressed in the mammary gland and secreted into the milk of said mammal, and wherein said expression is at a higher level than when said first DNA sequence is introduced in the absence of said second DNA sequence; and (b) collecting the milk produced in step (a) and isolating said protein of interest.

8. A method as in claim 7, wherein the first DNA sequence encoding said protein is cDNA.

9. A method as in claim 7, wherein the first DNA sequence encoding said protein is isolated from a milk protein gene.

10. A method as in claim 9, wherein the first DNA sequence encoding said protein is isolated from the same gene sequence as the second DNA sequence.

11. A method as in claim 7, wherein the regulatory sequence is from a mammary gland specific gene isolated from the same species as the transgenic mammal.

12. A method as in claim 7, wherein the protein has pharmaceutical activity.

* * * * *